United States Patent [19]

Scherrer et al.

[11] 4,143,154

[45] Mar. 6, 1979

[54] ANTI-MICROBIAL 2-NITRO-3-PHENYL BENZOFURANS SUBSTITUTED BY CARBOXY CONTAINING GROUP

[75] Inventors: Robert A. Scherrer, White Bear Lake; Walton J. Hammar, St. Paul; Richard M. Stern, Cottage Grove, all of Minn.

[73] Assignee: Riker Laboratories, Inc., Northridge, Calif.

[21] Appl. No.: 861,891

[22] Filed: Dec. 19, 1977

[51] Int. Cl.$^2$ ................ A61K 31/345; C07D 307/82
[52] U.S. Cl. ............................... 424/285; 260/346.22
[58] Field of Search .................... 260/346.22; 424/285

[56] References Cited

U.S. PATENT DOCUMENTS

| 4,048,323 | 9/1977 | Scherrer | 260/346.22 |
| 4,066,782 | 1/1978 | Scherrer | 260/346.22 |
| 4,067,993 | 1/1978 | Scherrer | 260/346.22 |

FOREIGN PATENT DOCUMENTS 864502 3/1977 Belgium.

*Primary Examiner*—Henry R. Jiles
*Assistant Examiner*—Bernard Dentz
*Attorney, Agent, or Firm*—Cruzan Alexander; Donald M. Sell; Donald C. Gipple

[57] ABSTRACT

Acidic 2-nitro-3-phenylbenzofurans and their pharmaceutically acceptable salts which are active as antimicrobial agents, processes for their use and intermediates therefor are described.

7 Claims, No Drawings

ANTI-MICROBIAL 2-NITRO-3-PHENYL BENZOFURANS SUBSTITUTED BY CARBOXY CONTAINING GROUP

BACKGROUND OF THE INVENTION

The present invention relates to a class of compounds wherein 2-nitro-3-phenylbenzofuran is substituted by an acidic group which are active antimicrobial agents, to processes for their use and to intermediates in their preparation.

Compounds wherein 2-nitro-3-phenylbenzofuran is substituted by an alkanoic acid are known and are known to have antimicrobial activity (see, for example, Belgian Pat. No. 846,502 and German Offenlegungsschrift No. P 2642877). However, the known compounds contain only a single alkanoic acid group and it is always substituted on the 3-phenylbenzofuran system. The compounds of the present invention, on the other hand, either include a second alkanoic acid group bonded to the benzo ring or the substituent acidic groups therein are linked by heteroatoms (oxygen or sulfur), are substituted by hydroxy or phenyl, or contain two carboxylic groups.

DETAILED DESCRIPTION OF THE INVENTION

The compounds of the present invention contain a 2-nitro-3-phenylbenzofuran structure substituted by two separate alkanoic acid functions or, alternatively, on the benzo ring of the benzofuran by an oxyalkanoic, α-hydroxyalkanoic, methylthioacetic, α-phenylacetic, methyloxyphenylalkanoic, methylenemalonic or methylmalonic acid function.

The invention also relates to pharmaceutically acceptable salts of the compounds, to the use of the compounds and salts as antimicrobial agents and to certain synthetic intermediates useful for their preparation.

More specifically, the invention relates to compounds of the formula

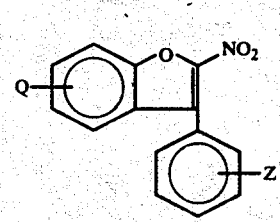

I wherein
Q is —CH$_2$COOH,

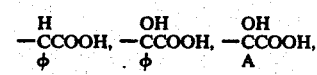

—CH$_2$OCH$_2$COOH, —CH$_2$OφCH$_2$COOA, —CH$_2$SCH$_2$COOH, —OCH$_2$COOH, —CH$_2$CH(COOR)$_2$ or —CH=C(COOR)$_2$,

Z is H except that when Q is —CH$_2$COOH, Z is COOH,

A is H, CH$_3$ or C$_2$H$_5$ and

R is H or lower alkyl and pharmaceutically acceptable salts thereof.

The pure compounds of the invention are generally white, yellow or yellow-green solids. Most are crystalline. They are substantially insoluble in water and aliphatic hydrocarbons and are more soluble in acetone, lower alkanols, N,N-dimethylformamide, benzene and the like. The esters are generally somewhat more soluble in organic solvents. The alkali metal salts have appreciable solubility in water and lower alcohols.

All of the compounds of the invention are active against bacteria and some are also active against other microorganisms, including fungi and protozoa, in vitro and topically. Thus, they can be used for disinfecting and sterilizing, for example of medical and dental equipment, as components of disinfecting solutions. The compounds are particularly useful as antibacterial agents. Some of the compounds are also active in vivo in animals. The free acids are presently preferred for many purposes due to their gradually higher levels of antimicrobial activity in vitro. For applications in which water solubility is of importance, the salts are ordinarily used.

The compounds of the invention in which Z is hydrogen are presently preferred. Other preferred subclasses of the compounds of the invention are those in which Q is —CH$_2$CH(COOR)$_2$ and —CH=C(COOR)$_2$ and in which A is hydrogen. Q is preferably in the 5, 6 or 7 position of the benzofuran moiety of the compounds of the invention.

The compounds of formula I in which Q is —CH$_2$COOH and Z is —COOH are prepared utilizing the following reaction sequence:

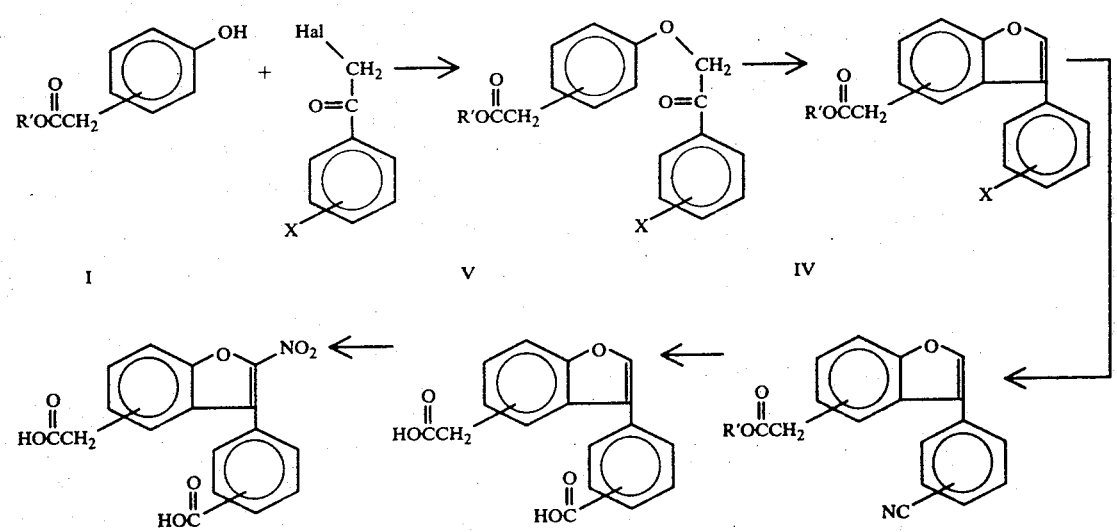

wherein R' is hydrogen or preferably lower alkyl, Hal is chloro or bromo and X is bromo, chloro or iodo. The starting substituted phenols and dihaloacetophenones are known or prepared by conventional means. Certain of the compounds II and III are also known. The condensates II are generally prepared at reflux in an inert solvent such as benzene, acetone and the like in the presence of a weak base such as sodium or potassium carbonate and are cyclized by heating in the presence of polyphosphoric acid to form the compounds III. The halogen is then displaced by reaction with cuprous cyanide in a solvent such as pyridine or quinoline by heating at 125°–200° C. to provide the novel 3-(cyano)-phenylbenzofuranacetic acid ester. The cyano group of this product is converted to a carboxy group and the ester of the acetic acid is hydrolyzed by heating with strong inorganic base.

In order to prepare the final products of the invention which are substituted in the 2 position by a nitro group, various methods for nitrating the 2 position, before or after other substituents are introduced, are used. These methods are described generally in several patents in the art and are specifically exemplified in the example section hereof.

The compounds of formula I in which Q is

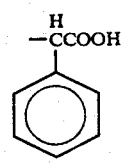

are prepared by means of the following sequence:

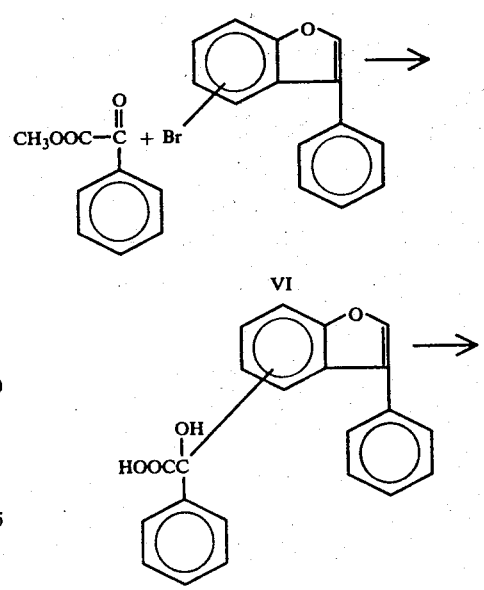

-continued

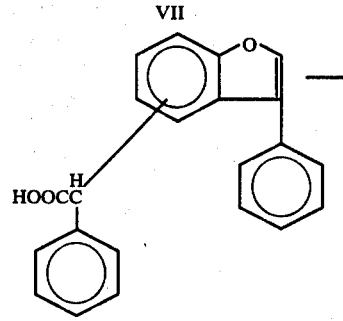

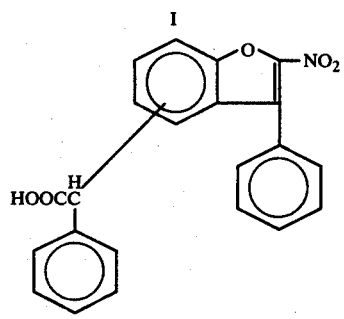

The corresponding 4,5,6 or 7-bromo-3-phenylbenzofurans are converted to Grignard reagents which are reacted with methyl benzoyl formate under standard Grignard conditions to form the novel α-3-diphenylbenzofuran glycolic acids VI. These compounds are refluxed with red phorphorus and hydrogen iodide in an inert solvent such as toluene in the presence of acetic anhydride to replace the α-hydroxy group, and these novel intermediates are nitrated to provide compounds of formula I.

The compounds of formula I in which Q is

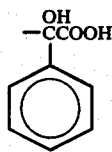

are prepared from the condensates VI above either by direct nitration or through the 2-bromo intermediate.

The compounds of formula I in which Q is

can be prepared alternatively by nitration of the 2 position of the comparable 2-unsubstituted compounds or by converting the 2-nitro-3-phenylbenzofuranaldehydes to the corresponding cyanohydrins by reaction with an alkali metal cyanide and then hydrolyzing those compounds to the desired α-hydroxy acids by refluxing with acid (e.g. concentrated hydrochloric acid).

The compounds of formula I in which Q is —CH$_2$OCH$_2$COOH,

or —CH$_2$SCH$_2$COOH are prepared starting with 4,5,6 or 7-methyl-3-phenylbenzofurans. These compounds are brominated with N-bromosuccinimide in an inert solvent such as carbon tetrachloride. Using a sunlight lamp, peroxide catalyst and cobalt stearate, the 2 position and the alkyl group are both brominated. The bromomethyl-2-bromo-3-phenylbenzofuran intermediates obtained are then used to prepare the compounds of the invention by reaction with HOCH$_2$COOH,

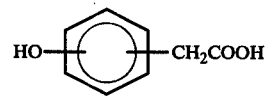

or HSCH$_2$COOH or the corresponding lower alkyl esters. These reactions are carried out in the presence of an organic base such as triethylamine or an inorganic base such as sodium or potassium hydroxide or sodium ethoxide in aqueous ethanol, ethanol, dichloromethane or any other suitable solvent. The 2-bromo group may in some cases be replaced first by a nitro group using the known methods, or the 2-bromo group may be replaced after the bromomethyl bromine has been reacted.

The compounds of formula I in which Q is —OCH$_2$COOH are prepared from the corresponding 4,5,6 or 7-hydroxy-3-phenylbenzofurans. These are reacted with reactive α-haloacetic acids (such as α-chloroacetic acid) or the corresponding esters to provide the novel oxyacetic-3-phenylbenzofurans

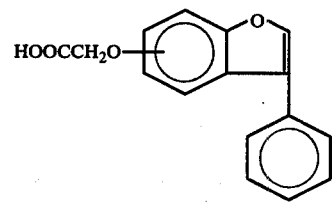

which are then converted to 2-nitro compounds by nitrating directly or by preparing the novel 2-bromo derivatives

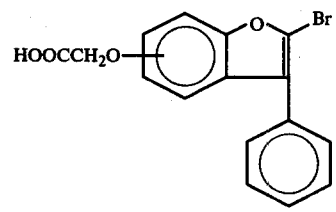

as intermediates and then nitrating those compounds as explained elsewhere herein.

The compounds of formula I in which Q contains two carboxylic groups are prepared from known 2-nitro-3-phenylbenzofuranaldehydes by condensation with dimethyl or diethyl malonate in the presence of base, generally by heating in an inert solvent such as benzene. The reaction rate may be accelerated by removing water as it is formed. This reaction provides compounds of the type

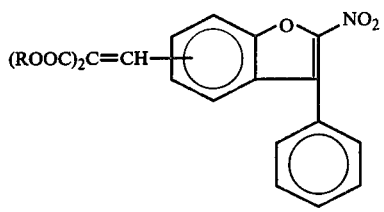

wherein the R groups are lower alkyl. These compounds can, in turn, be reduced using a metal hydride (such as sodium borohydride) to the corresponding compounds

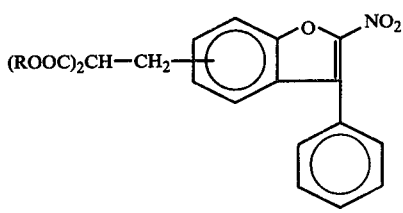

In order to obtain acids and salts from these esters, hydrolysis with strong inorganic base such as sodium or potassium hydroxide is utilized. In some cases hydrolysis prior to introduction of the nitro group is preferred.

The pharmaceutically acceptable salts of the invention are readily prepared by reaction of the corresponding free acids with the appropriate base and optionally in a suitable solvent and evaporation to dryness. The base used to prepare the salts may be organic, e.g. sodium methoxide or an amine, or inorganic. Furthermore, other salts which are not pharmaceutically acceptable may be useful for the synthesis of the acid compounds or other, acceptable salts or other useful intermediates such as esters.

The antimicrobial activity of the compounds is evaluated using a variation of the original agar-plate diffusion method of Vincent and Vincent (e.g. see Vincent, J. G., and Vincent, Helen W., Proc. Soc. Exptl. Biol. Med. 55:162–164, 1944, and David, B. D., and Mingioli, E. S., J. Bac. 66:129–136, 1953). Using this test, the compounds of the invention have been found to have a broad spectrum of activity against both gram-positive and gram-negative microorganisms. The procedure provides information on the amount of a compound required to give complete inhibition, partial inhibition or no inhibition of microbial growth on agar plates. The microbial growth on each plate if read visually, and minimal inhibitory concentrations are recorded.

The microorganisms used are: *Staphylococcus aureus, Bacillus subtilus, Pseudomonas aeruginosa, Escherichi coli, Streptococcus* sp. (strains isolated from dental caries in rats or hamsters at the National Institute of Dental Health and grown in PFY or APT agar), *Asperigillus niger, Candida albicans, Mima polymorpha, Herellea vaginicola, Klebsiella pneumoniae* and *Streptococcus fecaelis.*

These are selected representatives of various bacterial and fungal classes and broad spectrum activity can be predicted as a result of activity against them. All of the compounds of the invention possess antimicrobial activity towards one or more of the above microorganisms. The compounds maintain high activity against the microorganisms either in the absence or presence of ten percent horse serum.

The in vivo antimicrobial activity is determined against infections produced by *Streptococcus pyogenes* C-203 and *Staphylococcus aureus* (Smith) or other bacterial species. The species used is determined by the in vitro antimicrobial spectrum of the compound. Groups of five or ten mice, 18–22 g., are infected intraperitoneally with the test culture. Treatment consists of three oral injections 1, 6 and 24 hours after infection. All mice are observed for extended periods, e.g. for two weeks and deaths recorded at daily intervals. Control groups consist of one infected, nontreated group and other infected groups receiving varying dosages of the reference standard.

The acute oral toxicity of the compounds of the invention generally is moderate to low compared with the effective oral dose, and they have a good to excellent therapeutic ratio.

The compounds of the invention may be formulated by incorporating them into conventional pharmaceutical carrier materials, either organic or inorganic, which are suitable for oral or intraperitoneal application. For in vitro or topical use, simple aqueous solutions or suspensions are most conveniently employed. For this purpose, concentrations of the order of 100 parts per million up to about 5 parts per thousand are suitable, and the formulation is used by immersing the object to be treated therein, or by local application to an infected area. The amount of compound to be used for e.g. oral treatment of a microbial infection will be an effective amount less than a toxic amount. The amount to be administered to a subject and route of administration to control an infection will depend on the species of organism, the sex, weight, physical condition of the subject, the locus of the infection, and many other factors, but this judgment is well within the skill of the art. Usually the amount will be less than 100 mg/kg per dose. Conveniently the oral treatment is administered in the form of the usual pharmaceutical preparations such as capsules, tablets, emulsions, solutions, suppositories and the like. Excipients, fillers, coatings, etc. are employed with tablets or capsules, as is well known in the art.

It is often advantageous to combine the compounds of this invention with other antimicrobial compounds such as coccidiostats, anthelmintics, antifungals, antibiotics, steroids, or antibacterial agents, or to combine more than one compound described herein in a single composition.

Certain of the compounds are also active antiparasitics as shown by activity in laboratory tests versus the protozoan *Trichomonas sp.* In view of the outstanding antimicrobial activity of the compounds, they would also be expected to be effective growth promoters in various animal and bird species.

The following examples are given for the purpose of further illustrating the procedures of the present invention, but are not intended, in any way, to be limiting on the scope thereof. The melting points are uncorrected and the temperatures are in degrees Centigrade.

EXAMPLE 1

Step A. A mixture of the known (U.S. Pat. No. 3,862,134) compound 2-hydroxy-2-[7-(3-phenylbenzofuran)]propionic acid (1.8 g., 0.00638 mole) and 250 ml. of dichloromethane is treated dropwise with 1.03 g. (0.0064 mole) of bromine, and the mixture is stirred at 20° C. for about 25 minutes. The solution is evaporated to provide a white solid residue. The product is 2-hydroxy-2-[7-(2-bromo-3-phenylbenzofuran)]propionic acid, m.p. 152°–155° C.

Step B. The product of step A is dissolved in 200 ml. of acetic acid by warming. To this solution is added 3.4 ml. of nitric acid, then 0.8 g. of sodium nitrite gradually over about 30 seconds. The mixture is gradually heated to 80° C. over 20 minutes, then maintained at 80° C. for 40 additional minutes. The mixture is poured into water, then extracted with diethyl ether. The ether extracts are washed with water, then with a saturated sodium chloride solution, and dried. The ether solution is evaporated. The residue is treated with benzene and evaporated. The solid is recrystallized from benzene to provide 2-hydroxy-2-[7-(2-nitro-3-phenylbenzofuran)]propionic acid, m.p. 184°–187° C.

Analysis: %C; %H; %N; Calculated for $C_{17}H_{13}NO_6$: 62.5; 4.0; 4.3; Found: 62.1; 3.9; 4.3.

EXAMPLE 2

Using the method of Example 1, and starting with 2-hydroxy-2-[5-(3-phenylbenzofuran)]propionic acid (m.p. 154°–157° C., prepared by the process of U.S. Pat. No. 3,862,134) the product obtained by recrystallization from benzene is yellow crystals of 2-hydroxy-2-[5-(2-nitro-3-phenylbenzofuran)]propionic acid, m.p. 158°–161° C.

Analysis: %C; %H; %N; Calculated for $C_{17}H_{13}NO_6$: 62.5; 4.0; 4.3; Found: 62.9; 4.1; 4.1.

EXAMPLE 3

To a solution of 10 g. (0.0375 mole) of 2-nitro-3-phenyl-7-benzofuranaldehyde (described in Belgian Pat. No. 846,502, Example 13) in 30 ml. of benzene is added 5.7 g. (0.0355 mole) of diethyl malonate, 0.15 g. of 2-nitro-3-phenylbenzofuran-7-carboxylic acid and 0.2 ml. of piperidine. The mixture is heated at its reflux temperature with stirring using a Dean-Stark trap and condenser for nine hours. The mixture is added to 100 ml. of benzene and 100 ml. of water and mixed thoroughly, the benzene layer is separated, washed with water, then twice with 1N hydrochloric acid, then with 100 ml. of a saturated sodium bicarbonate solution. The organic layer is dried, then evaporated to provide a residue which is recrystallized from a mixture of cyclohexane and benzene to provide yellow crystals of diethyl 2-nitro-3-phenyl-7-benzofuranylmethylenemalonate, m.p. 139°–140.5° C.

Analysis: %C; %H; %N; Calculated for $C_{22}H_{19}NO_7$: 64.5; 4.7; 3.4; Found: 64.8; 4.6; 3.4.

EXAMPLE 4

Step A. To a mixture of 0.76 g. (0.02 mole) of sodium borohydride in 50 ml. of ethanol and 30 ml. of glyme is added 8 g. (0.0196 mole) of diethyl 2-nitro-3-phenyl-7-benzofuranylmethylenemalonate in 100 ml. of glyme at a temperature of 0°–5° C. over a period of about 20 minutes. The mixture is stirred at about 5° C. for one hour then at 20° C. for about two hours. The mixture is poured into 800 ml. of water, then extracted with diethyl ether. The ether extracts are washed with water, saturated sodium chloride solution and dried. The solution is evaporated to provide a residue which is dissolved in trichloroethylene and cooled. The precipitate is separated by filtration and the filtrate is evaporated to dryness to provide a residue which is purified by column chromatography on florisil, using benzene then ethanol to elute. The product is diethyl 2-nitro-3-phenyl-7-benzofuranylmethylmalonate.

Step B. A solution of 5.7 g. of the product of step A and 50 ml. of ethanol is treated with 5.7 g. of potassium hydroxide dissolved in 5.7 ml. of water. The mixture is refluxed on a steam bath for ½ hour. The solution is evaporated, water is added, and the mixture is filtered. The aqueous solution is acidified, and the yellow solid product is separated by filtration and washed with water. The product is recrystallized from a mixture of water and ethanol, then from water to provide light yellow solid monopotassium 2-nitro-3-phenyl-7-benzofuranylmethylmalonate hemihydrate, m.p. 162°–168° C.

Analysis: %C; %H; %N; Calculated for $C_{18}H_{12}KNO_7 \cdot 1/2\ H_2O$: 53.8; 3.3; 3.5; Found: 53.7; 3.3; 3.5.

The anhydrous compound can be recovered using known techniques.

EXAMPLE 5

Step A. To a solution of 112 g. (0.538 mole) of 5-methyl-3-phenylbenzofuran in 500 ml. of carbon tetrachloride is added 192 g. (1.076 mole) of N-bromosuccinimide and 0.1 g. of benzoyl peroxide. The mixture is heated at reflux with a sunlamp for one hour, then 0.5 g. of tertiary-butyl peroxide and 0.5 g. of cobalt stearate are added. After an additional three hours of heating and stirring the mixture is allowed to come to a temperature of 20° C. and is filtered. The filtrate is evaporated to provide an oily yellow solid which crystallizes when scratched in petroleum ether to provide 2-bromo-5-bromomethyl-3-phenylbenzofuran.

Step B. To a solution of 50 g. (0.137 mole) of the product of step A in 1100 ml. of acetic acid is added 18.9 g. (0.206 mole) of dinitrogen tetraoxide and 26.0 g. (0.206 mole) of 4-cyclohexene carboxylic acid in 25 ml. of acetic acid dropwise. The reaction mixture is maintained at 45° C. for about four hours, then allowed to cool to about 20° C. The yellow solid is collected, washed with water and petroleum ether and dried to provide 5-bromomethyl-2-nitro-3-phenylbenzofuran, crude melting point 171°–180° C.

Step C. To a solution of 5.5 g. (0.017 mole) of the product of step B in 100 ml. of ethanol is added 1.8 g. (0.02 mole) of α-mercaptoacetic acid, 1.4 g. (0.034 mole) of sodium hydroxide in 20 ml. of water. The mixture is heated to its reflux temperature and maintained at reflux for about three hours. The mixture is cooled to about 20° C., then filtered. The filtrate is concentrated, the residue is diluted with water, then extracted with dichloromethane. The dichloromethane extracts are washed with water, dried, then concentrated to provide a thick yellow oil. The oil is dissolved in dichloromethane, and 100 ml. of cold 5 percent sodium hydroxide solution is added. A yellow solid precipitates which is collected and dried, then recrystallized from water. After thorough drying, the product obtained is sodium 2-(2-nitro-3-phenyl-5-benzofuranylmethylmercapto)acetate dihydrate, m.p. 174°–180° C.

Analysis: %C; %H; %N; Calculated for $C_{17}H_{16}O_7NNaS$: 50.9; 4.0; 3.5 Found: 50.9; 3.9; 3.7.

The anhydrous compound can be recovered using known techniques.

EXAMPLE 6

To a solution of 7.2 g. (0.0176 mole) of the product of Example 3 in 50 ml. of ethanol, 25 ml. of diethyl ether, and 25 ml. of benzene is added a solution of 1.0 g. of potassium hydroxide in 8 ml. of ethanol. The mixture is stirred at about 20° C. for about 16 hours. The mixture is filtered, and the solid is washed twice with benzene, then twice with diethyl ether. All of the filtrates are combined, then evaporated to provide a residue. The residue is suspended in warm water, treated with decolorizing charcoal and filtered. The filtrate is washed with diethyl ether, then cooled and carefully acidified. The aqueous mixture is then extracted with diethyl ether, the ether extracts are washed twice with water, twice with saturated sodium chloride solution, and dried. The extracts are evaporated to provide a residue. The residue is suspended in carbon tetrachloride and gradually forms a solid which is recrystallized from benzene to provide ethyl hydrogen 2-nitro-3-phenyl-7-benzofuranylmethylenemalonate, m.p. 213.5°–216.5° C.

Analysis: %C; %H; %N; Calculated for $C_{20}H_{13}NO_7$: 63.0; 4.0; 3.7; Found: 63.0; 4.0; 3.6.

EXAMPLE 7

A solution of 0.55 g. (0.0072 mole) of glycolic acid and 0.73 g. (0.0072 mole) of triethylamine in 100 ml. of dichloromethane is stirred for 30 minutes. To this solution is added 2 g. (0.006 mole) of 5-bromomethyl-2-nitro-3-phenylbenzofuran (described in Belgian Pat. No. 846,502, Example 19), and the mixture is heated at its reflux temperature for about 80 hours. The mixture is evaporated, and the residue is dissolved in 150 ml. of toluene. To this solution is added 0.3 g. of triethylamine, and the mixture is heated at its reflux temperature for 16 hours. The mixture is filtered and washed with water. The organic layer is dried, then evaporated. The residue is eluted through a silica gel column with benzene. The solid obtained is a yellow powder, 4-(2-nitro-3-phenylbenzofuran-5-yl)-3-oxabutyric acid, m.p. 128°–129° C.

Analysis: %C; %H; %N; Calculated for $C_{17}H_{13}NO_6$: 62.4; 4.0; 4.3; Found: 62.0; 4.0; 4.2.

EXAMPLE 8

Step A. To a solution of 0.0041 mole of sodium ethoxide in 150 ml. of ethanol is added 7.5 g. (0.0041 mole) of ethyl 4-hydroxyphenylacetate in 50 ml. of ethanol over 30 minutes while at 20° C. The mixture is cooled and stirred at 0° C. for two hours, then 15 g. (0.041 mole) of 2-bromo-5-bromomethyl-3-phenylbenzofuran in 50 ml. of ethanol is added. The mixture is stirred at 20° C. for 16 hours, then heated to 50° C. for about 18 hours. The mixture is cooled to 20° C. and evaporated to provide a residue. The residue is extracted with chloroform, and the chloroform extracts are washed with water, then dried. The extracts are evaporated, then chromatographed through silica gel with carbon tetrachloride as the eluent. The product obtained is ethyl 4-[(2-bromo-3-phenylbenzofuran-5-yl)methoxy]phenylacetate.

Step B. To a stirred solution of 2 g. (0.0043 mole) of the product of step A in 100 ml. of dichloromethane and 1.08 g. (0.0086 mole) of dinitrogen tetraoxide in 10 ml. of dichloromethane. The solution is stirred for about 20 hours, washed with two portions of 10 percent sodium carbonate solution and two portions of water, then dried. The solution is evaporated, the residue is chromatographed on silica gel, eluting with benzene. The early fractions contain the desired product which is recrystallized from a mixture of hexane and benzene to provide ethyl 4-[(2-nitro-3-phenylbenzofuran-5-yl)methoxy]phenylacetate, m.p. 74°–75° C.

Analysis: %C; %H; %N; Calculated for $C_{25}H_{21}NO_6$: 69.6; 4.9; 3.2; Found: 69.6; 5.0; 3.1.

EXAMPLE 9

To a solution of 0.0066 ml. of sodium ethoxide in 50 ml. of ethanol is added 1.2 g. (0.0066 mole) of ethyl 3-hydroxyphenylacetate. The mixture is heated at its reflux temperature for three hours, then 2 g. (0.006 mole) of 5-bromomethyl-2-nitro-3-phenylbenzofuran is added. The mixture is heated at its reflux temperature for 16 hours. On cooling of the reaction mixture a yellow precipitate is obtained which is separated by filtration. Recrystallization from a mixture of hexane and benzene provides ethyl 3-[(2-nitro-3-phenylbenzofuran-5-yl)methoxy]phenylacetate, m.p. 67°–68° C.

Analysis: %C; %H; %N; Calculated for $C_{25}H_{21}NO_6$: 69.6; 4.9; 3.2; Found: 69.8; 4.9; 3.3.

EXAMPLE 10

To a mixture of 1 g. (0.0066 mole) of 4-hydroxyphenylacetic acid and 0.53 g. of sodium hydroxide in 100 ml. of ethanol is added 2 g. (0.006 mole) of 5-bromomethyl-2-nitro-3-phenylbenzofuran, and the mixture is heated at its reflux temperature for 16 hours. The reaction mixture is evaporated to provide a residue which is extracted thoroughly with chloroform. The residue is separated from chloroform and dissolved in water. The water is acidified to pH 3. The precipitate is separated by filtration, dissolved in dichloromethane, and the dichloromethane solution is dried. The dichloromethane solution is evaporated to provide a yellow solid which is recrystallized from ethanol to provide 4-[(2-nitro-3-phenylbenzofuran-5-yl)methoxy]phenylacetic acid, m.p. 179°–180° C.

Analysis: %C; %H; %N; Calculated for $C_{23}H_{17}NO_6$: 68.5; 4.2; 3.5; Found: 68.7; 4.3; 3.4.

EXAMPLE 11

Using the method of Example 10 and starting with 2-hydroxyphenylacetic acid and 5-bromomethyl-2-nitro-3-phenylbenzofuran a product is obtained which is purified by chromatography on silica gel, eluting with chloroform. The yellow solid obtained is 2-[(2-nitro-3-phenylbenzofuran-5-yl)methoxy]phenylacetic acid, m.p. 223°–224° C.

Analysis: %C; %H; %N; Calculated for $C_{23}H_{17}NO_6 \cdot 1/2 H_2O$: 67.0; 4.4; 3.4; Found: 67.1; 4.3; 3.3.

EXAMPLE 12

Using the method of Example 10 and starting with 3-hydroxyphenylacetic acid and 5-bromomethyl-2-nitro-3-phenylbenzofuran the product obtained is recrystallized from ethanol to provide 3-[(2-nitro-3-phenylbenzofuran-5-yl)methoxy]phenylacetic acid, m.p. 144°–145° C.

Analysis: %C; %H; %N; Calculated for $C_{23}H_{17}NO_6$: 68.5; 4.2; 3.5; Found: 68.1; 4.4; 3.5.

EXAMPLE 13

Step A. A mixture of 99 g. (0.29 mole) of the known (Belgian Pat. No. 846,502, Example 22) compound ethyl 3-(4-bromophenyl)benzofuran-5-acetate in 40 g. of cuprous cyanide in 30 ml. of pyridine is heated at 160°–175 C. with stirring under a nitrogen atmosphere for 20 hours. To this solution is added 200 g. of ferric chloride, 100 ml. of concentrated hydrochloric acid, and 200 ml. of ice water with rapid stirring. Next, 300 ml. of chloroform is added, and the mixture is stirred for one hour, then filtered, and the insoluble material is extracted several times with chloroform. The combined chloroform extracts are dried and evaporated to provide a residue. The residue is recrystallized from a N,N-dimethyl formamide-water mixture to provide ethyl 3-(4-cyanophenyl)benzofuran-5-acetate.

Step B. A mixture of 5 g. of the product of step A in 50 ml. of 30 percent sodium hydroxide solution and 20 ml. of ethanol is heated at its reflux temperature for 30 minutes, and 75 ml. of water is added. The solution is heated at its reflux temperature for three hours, then poured into 125 ml. of 6N hydrochloric acid. The solid is separated by filtration and recrystallized from acetic acid to provide 3-(4-carboxyphenyl)benzofuran-5-acetic acid, m.p. 278°–281° C.

Analysis: %C %H Calculated for $C_{17}H_{12}O_5$: 68.9; 4.1 Found: 68.2; 4.0.

Step C. To a suspension of 2 g. of the product of step B in 10 ml. of acetonitrile is added 0.2 g. of cupric nitrate hydrate and 1 g. of dinitrogen tetraoxide in 2 ml. of acetonitrile. The mixture is stirred at 20° C. for two hours, 0.5 g. of additional dinitrogen tetraoxide is added, and the mixture is stirred for an additional 18 hours. It is then concentrated, and the solid is separated by filtration and recrystallized from acetic acid to provide light yellow crystals of 3-(4-carboxyphenyl-2-nitrobenzofuran-5-acetic acid, m.p. 290° C. (dec.).

Analysis: %C; %H; %N; Calculated for $C_{17}H_{11}NO_7$: 59.8; 3.3; 4.1; Found: 59.5; 3.3; 4.0.

EXAMPLE 14

Step A. A stirred mixture of 2.7 g. (0.010 mole) of 2-nitro-3-phenylbenzofuran-7-aldehyde and 20 ml. of diethyl ether is treated with 1.6 g. (0.015 mole) of sodium bisulfite in 10 ml. of water. After 30 minutes, 30 ml. of chloroform is added and then, 30 minutes later, 1.5 g. (0.030 mole) of sodium cyanide in 5 ml. of water is added. One-half hour after that 0.7 g. of sodium bisulfite is added, then, after another 30 minutes, the mixture is cooled at 0° C. for about 16 hours. The organic layer is separated, washed with aqueous sodium bisulfite solution, then with water, and dried over magnesium sulfate. Evaporation of the solution provides a solid which is recrystallized from a chloroform-heptane mixture to provide yellow crystals of α-hydroxy-2-nitro-3-phenylbenzofuran-7-acetonitrile, m.p. 137°–139° C.

Analysis: %C; %H; %N; Calculated for $C_{16}H_{10}N_2O_4$: 65.3; 3.4; 9.5; Found: 64.9; 3.3; 9.5.

Step B. A mixture of 1 g. of the product of step A and 20 ml. of concentrated hydrochloric acid is heated on a steam bath for two hours. The mixture is evaporated to provide a residue which is recrystallized from a mixture of acetic acid and water to provide 2-nitro-3-phenylbenzofuran-7-glycolic acid, m.p. 113°–118° C. (dec.).

Analysis: %C; %H; %N; Calculated for $C_{16}H_{11}NO_6 \cdot 1/3 \ H_2O$: 60.2; 3.7; 4.4; Found: 60.2; 3.6; 4.7.

EXAMPLE 15

Step A. 2-Nitro-3-phenylbenzofuran-5-carboxaldehyde (prepared according to the method of Belgian Pat. No. 846,502) is reacted (by the method of step A of Example 14 hereof) to provide α-hydroxy-2-nitro-3-phenylbenzofuran-5-acetonitrile.

Step B. A mixture of 5.4 g. of the product of step A and 50 ml. of concentrated hydrochloric acid is heated at its reflux temperature for two hours. The liquid is poured away from the residue, and the residue is recrystallized from a mixture of isopropyl alcohol and water to provide 2-nitro-3-phenylbenzofuran-5-glycolic acid, m.p. 158°–161° C.

Analysis: %C; %H; %N; Calculated for $C_{16}H_{11}NO_6$: 62.4; 4.0; 4.3; Found: 62.9; 4.1; 4.1.

EXAMPLE 16

Step A. A mixture of 2.1 g. of magnesium and 25 ml. of tetrahydrofuran is treated with several drops of methylmagnesium bromide then with several drops of dibromopropane, and the mixture is heated at its reflux temperature. To this mixture is added 20.8 g. (0.076 mole) of 5-bromo-3-phenylbenzofuran over a period of ten minutes. The mixture is heated at its reflux temperature for 1.5 hours, then cooled. This mixture is slowly added to a solution of 25 g. (0.152 mole) of methyl benzoylformate in 75 ml. of tetrahydrofuran while stirring at −50° C. over a period of ten minutes. The reaction mixture is allowed to warm gradually to 20° C. over a period of 16 hours. To this mixture is added 20 ml. of 6N hydrochloric acid, and the mixture is stirred for 30 minutes. The layers are separated and the aqueous layer is extracted with chloroform. The chloroform extracts are combined with the tetrahydrofuran layer, the organic layers are washed with saturated sodium chloride solution and dried. The extracts are then evaporated to provide a residue which is dissolved in 75 ml. of ethanol. To this mixture is added 25 ml. of 50 percent sodium hydroxide solution and 20 ml. of water, and the mixture is heated on a steam bath for two hours. The ethanol is removed by evaporation, and additional water is added. The aqueous solution is washed with diethyl ether, treated with decolorizing charcoal and filtered. To the aqueous solution is then added dropwise over three hours dilute hydrochloric acid. A solid separates which is isolated by filtration and recrystallized from acetic acid to provide brown crystals of α-3-diphenylbenzofuran-5-glycolic acid, m.p. 160°–162° C. (dec.).

Analysis: %C; %H; Calculated for $C_{22}H_{16}O_4$: 76.7; 4.7; Found: 76.0; 4.7.

Step B. To a refluxing solution of 1.5 g. (0.0043 mole) of the product of step A in 10 ml. of toluene with 0.1 g. of red phosphorous is added a mixture of 2.0 g. of 55 percent hydrogen iodide and 1 ml. of acetic anhydride over a period of one hour. The mixture is heated at its reflux temperature for an additional three hours then cooled, a dilute solution of sodium metabisulfite is added, and stirred at 20° C. for one hour. The solution is evaporated to provide a residue which is recrystallized from a dichloromethane heptane mixture to provide white crystals of α-3-diphenylbenzofuran-5-acetic acid, m.p. 149°–153° C.

Analysis: %C; %H; Calculated for $C_{22}H_{16}O_3 \cdot 1/3 \ H_2O$: 79.0; 5.0; Found: 78.8; 4.8.

Step C. To a solution of 1 g. (0.003 mole) of the product of step B in 50 ml. of dichloromethane is added 0.16 ml. (0.003 mole) of bromine in 5 ml. of dichloromethane over a period of ten minutes. The mixture is stirred for 30 minutes, then concentrated to provide a residue which is dissolved in 50 ml. of chloroform. To this solution is added 0.5 g. of dinitrogen tetraoxide, and the mixture is stirred for one hour then evaporated to provide a residue which is recrystallized from a mixture of dichloromethane and heptane to provide green crystals of α-3-diphenyl-2-nitrobenzofuran-5-acetic acid, m.p. 90° C. (dec.).

Analysis: %C; %H; %N; Calculated for C$_{22}$H$_{15}$NO$_5$.1/3 CH$_2$Cl$_2$: 66.7; 3.9; 3.5; Found: 66.1; 3.9; 3.2.

EXAMPLE 17

Step A. A solution of 10 g. (0.048 mole) of 6-hydroxy-3-phenylbenzofuran, 5.7 g. (0.006 mole) of chloroacetic acid and 4.8 g. (0.12 mole) of sodium hydroxide in 100 ml. of water is heated at its reflux temperature for 2.5 hours, and an additional 10 percent of the original amounts of chloroacetic acid and sodium hydroxide are added. The reaction mixture is refluxed for an additional 24 hours then poured into 600 ml. of hot water, and the hot mixture is acidified with 6N hydrochloric acid. The precipitate is collected, washed with water, and dissolved in diethyl ether. The ether solution is washed twice with 100 ml. portion of 5 percent sodium bicarbonate solution. A white precipitate forms and is collected by filtration and dissolved in warm water. The aqueous solution is poured into cold dilute hydrochloric acid. The product is separated by filtration and dissolved in diethyl ether, the ether extracts are washed with water and saturated with sodium chloride solution, then dried. Evaporation provides a residue which is 3-phenyl-6-benzofuranyl oxyacetic acid, m.p. 153°–156° C.

Step B. To a stirred, refluxing solution of 6 g. (0.022 mole) of the product of step A in 700 ml. of dichloromethane is added 4.0 g. (0.025 mole) of bromine in 5 ml. of dichloromethane over a period of ten minutes. After refluxing for one hour, the solution is allowed to cool to 20° C. The precipitate, which is collected and washed with dichloromethane, is 2-bromo-6-benzofuranyloxyacetic acid, m.p. 184°–188° C.

Step C. To a solution of 3.5 g. (0.010 mole) of the product of step B in 400 ml. of acetic acid is added 1.3 g. (0.015 mole) of cyclohexane and 1.4 g. (0.015 mole) of dinitrogen tetraoxide in 20 ml. of acetic acid over 50 minutes. The reaction mixture is stirred for two hours, then poured into cold water. The product is separated by filtration and dissolved in diethyl ether, the ether is washed with water, then extracted with five portions of 10 percent sodium bicarbonate solution. The first three of these extractions form a precipitate which is collected by filtration, suspended in hot water, filtered to remove a small residue, then the filtrate is poured into cold dilute hydrochloric acid. The aqueous solution is extracted with dichloromethane, the dichloromethane extracts are washed with water and dried. Evaporation provides the yellow solid which is recrystallized from aqueous ethanol to provide bright yellow needles of 2-nitro-3-phenyl-6-benzofuranyloxyacetic acid, m.p. 189°–192° C. (dec.).

Analysis: %C; %H; %N; Calculated for C$_{16}$H$_{11}$O$_6$N.1/2 H$_2$O: 59.6; 3.8; 4.3; Found: 59.5; 3.7; 4.4.

EXAMPLE 18

Step A. A solution of 4.5 g. (0.013 mole) of α-3-diphenylbenzofuran-5-glycolic acid (the product of step A, Example 16) in 250 ml. of dichloromethane is treated with an equimolar amount of bromine over a ten minute period. After stirring for an additional 30 minutes, the solution is evaporated to provide a solid residue. Infrared spectral analysis is consistant with the product 2-bromo-α-3-diphenylbenzofuran-5-glycolic acid.

Step B. The product of step A is dissolved in 150 ml. of acetic acid, 6 ml. of nitric acid and 1.6 g. of sodium nitrite are added, and the mixture is heated on a steam bath for 45 minutes and stirred occasionally. The solution is allowed to stand at 20° C. for 16 hours, then poured into 500 ml. of water. The solution is extracted twice with diethyl ether, the ether solution is washed with saturated sodium chloride solution, dried and evaporated. The residue generally crystallizes from benzene to provide α-3-diphenyl-2-nitrobenzofuran-5-glycolid acid, m.p. 143°–145° C.

Analysis: %C; %H; %N; Calculated for C$_{22}$H$_{15}$NO$_6$: 67.9; 3.9; 3.6; Found: 67.7; 3.9; 3.5.

What is claimed is:

1. A compound of the formula

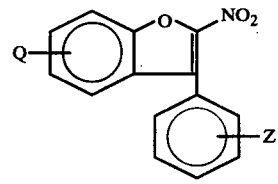

wherein
Q is —CH$_2$COOH,

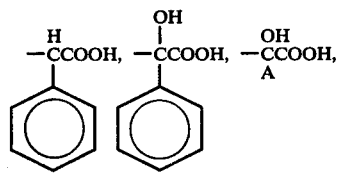

—CH$_2$OCH$_2$COOH,

—CH$_2$SCH$_2$COOH, —OCH$_2$COOH, —CH$_2$CH(COOR)$_2$ or —CH=C(COOR)$_2$,

Z is H except that when Q is —CH$_2$COOH, Z is COOH,

A is H, CH$_3$ or C$_2$H$_5$ and

R is H or lower alkyl and pharmaceutically acceptable salts thereof.

2. A compound according to claim 1 wherein Z is hydrogen.

3. A compound according to claim 2 wherein Q is —CH$_2$CH(COOR)$_2$.

4. A compound according to claim 2 wherein Q is —CH=C(COOR)$_2$.

5. A method for arresting or inhibiting the growth of miroorganisms comprising contacting microorganisms with a compound according to claim 1 in an amount sufficient to arrest or inhibit the growth of said microorganisms.

6. A method according to claim 5 for arresting or inhibiting the growth of bacteria.

7. A compound according to claim 1 wherein Q is on the 5, 6 or 7 position and Z is hydrogen.

* * * * *